(12) United States Patent
Kapiamba

(10) Patent No.: US 9,005,746 B2
(45) Date of Patent: Apr. 14, 2015

(54) POLYMERIC ASCORBIC ACID DEVICES FOR TISSUE REGENERATION

(71) Applicant: Covidien LP, Mansfield, MA (US)

(72) Inventor: Mbiya Kapiamba, Cromwell, CT (US)

(73) Assignee: Covidien LP, Mansfield, MA (US)

( * ) Notice: Subject to any disclaimer, the term of this patent is extended or adjusted under 35 U.S.C. 154(b) by 58 days.

(21) Appl. No.: 13/864,634

(22) Filed: Apr. 17, 2013

(65) Prior Publication Data

US 2013/0323511 A1 Dec. 5, 2013

Related U.S. Application Data

(60) Provisional application No. 61/653,527, filed on May 31, 2012.

(51) Int. Cl.
| | | |
|---|---|---|
| *A61L 27/34* | (2006.01) | |
| *A61L 27/58* | (2006.01) | |
| *C09D 175/02* | (2006.01) | |
| *C09D 175/04* | (2006.01) | |
| *A61L 31/10* | (2006.01) | |
| *A61L 31/16* | (2006.01) | |

(52) U.S. Cl.
CPC ............ *A61L 27/58* (2013.01); *A61L 31/10* (2013.01); *A61L 31/16* (2013.01); *A61L 27/34* (2013.01); *C09D 175/02* (2013.01); *C09D 175/04* (2013.01)

(58) Field of Classification Search
USPC .............. 428/319.3, 423.1; 427/2.14, 2.24; 524/589, 590
See application file for complete search history.

(56) References Cited

U.S. PATENT DOCUMENTS

| | | | |
|---|---|---|---|
| 4,326,523 | A | 4/1982 | Wolfrom et al. |
| 6,596,002 | B2 | 7/2003 | Therin et al. |
| 7,021,086 | B2 | 4/2006 | Ory et al. |
| 7,331,199 | B2 | 2/2008 | Ory et al. |
| 2003/0152556 | A1 | 8/2003 | Lai et al. |
| 2005/0013793 | A1 * | 1/2005 | Beckman et al. .......... 424/78.27 |
| 2005/0288789 | A1 | 12/2005 | Chaouk et al. |
| 2006/0155384 | A1 | 7/2006 | Ellingsen et al. |
| 2007/0160569 | A1 * | 7/2007 | Beckman et al. .......... 424/78.27 |
| 2007/0299542 | A1 | 12/2007 | Mathisen et al. |
| 2008/0262613 | A1 * | 10/2008 | Gogolewski ............... 623/11.11 |
| 2012/0202961 | A1 * | 8/2012 | Bhattacharyya et al. ....... 528/85 |

FOREIGN PATENT DOCUMENTS

JP  11079930 A  *  3/1999

* cited by examiner

*Primary Examiner* — Thao T Tran

(57) ABSTRACT

An implantable medical device is disclosed. The medical device includes a substrate and a polymer composition including ascorbic acid, the polymer composition disposed on at least a portion of the substrate.

18 Claims, 1 Drawing Sheet

POLYMERIC ASCORBIC ACID DEVICES FOR TISSUE REGENERATION

CROSS-REFERENCE TO RELATED APPLICATION

The present application claims the benefit of and priority to a U.S. provisional application Ser. No. 61/653,527, filed on May 31, 2012, the entire contents of which are incorporated by reference herein.

BACKGROUND

The present disclosure relates generally to implantable medical devices, and more particularly, to implantable medical devices which include at least one substrate and at least one polymeric composition including ascorbic acid disposed on at least a portion of the substrate.

Surgical meshes may be used during both laparoscopic and open surgery for repair of many types of defects and injuries. For example, surgical meshes are commonly used in the repair of hernias, pelvic organ prolapse and stress urinary incontinence.

During hernia repair, a mesh may be placed over the entirety of damaged tissue and some of the healthy tissue surrounding the defect. The mesh can be held in place by a fixation device that attaches the mesh to the surrounding tissue. A variety of different fixation devices may be used to anchor the mesh to the tissue. The mesh may further include an additional layer such as a film, for sustained delivery of analgesic agents to the vicinity of the mesh implant for reduction of acute post-operative pain. Integration of films to accommodate unique patient/anatomical features while maintaining the integrity of the film/mesh attachment is desired.

SUMMARY

According to one aspect of the present disclosure, an implantable medical device is disclosed. The medical device includes a substrate and a polymer composition including ascorbic acid, the polymer composition disposed on at least a portion of the substrate.

Additionally or alternatively, the polymer composition includes a polymer selected from the group consisting of polyurethanes, polyureas, and combinations thereof.

In further aspects of the present disclosure, the polymer includes an ascorbic acid isocyanate and a monomer selected from the group consisting of a polyol, a polyamine, an aminoalcohol, and combinations thereof.

According to another aspect of the present disclosure, an implantable medical device is disclosed. The medical device includes a substrate and a polymer composition including a polymer selected from the group consisting of polyurethanes, polyureas, and combinations thereof. The polymer includes an ascorbic acid isocyanate and a monomer selected from the group consisting of a polyol, a polyamine, an aminoalcohol, and combinations thereof. The polymer composition is disposed on at least a portion of the substrate.

A method for forming an implantable medical device is also contemplated by the present disclosure. The method includes contacting a substrate with a polymer composition including ascorbic acid, such that the polymer composition is disposed on at least a portion of the substrate.

In additional aspects, the method further includes contacting a substrate with a polymer composition including ascorbic acid, such that the polymer composition is disposed on at least a portion of the substrate.

In further aspects, the polymer composition includes a polymer selected from the group consisting of polyurethanes, polyureas, and combinations thereof.

In additional aspects, the method further includes contacting an ascorbic acid isocyanate with a monomer selected from the group consisting a polyol, a polyamine, an aminoalcohol, and combinations thereof to form the polymer.

A method for forming an implantable medical device is also contemplated by the present disclosure. The method includes contacting an ascorbic acid isocyanate with a monomer selected from the group consisting a polyol, a polyamine, an aminoalcohol, and combinations thereof to form a polymer selected from the group consisting of polyurethanes, polyureas, and combinations thereof and contacting a substrate with a polymer composition including the polymer, such that the polymer composition is disposed on at least a portion of the substrate.

Additionally or alternatively, in any of the above aspects of the present disclosure, the polymer composition includes a film.

Additionally or alternatively, in any of the above aspects of the present disclosure, the substrate is selected from the group consisting of a film, a coating, a sponge, a foam, a mesh, and combinations thereof.

Additionally or alternatively, in any of the above aspects of the present disclosure, the medical device includes at least one therapeutic agent.

Additionally or alternatively, in any of the above aspects of the present disclosure, the polyamine is selected from the group consisting of pentane-1,5-diamine, 3,3'-(cyclohexane-1,4-diyl)bis(propan-1-amine), 3-(aminomethyl)-3,5,5-trimethylcyclohexanamine, 1,3-phenylenedimethanamine, butane-1,3-diamine, cyclohexane-1,2-diamine, 2,3,4-trimethylhexane-1,6-diamine, N1-(3-aminopropyl)butane-1,4-diamine, 2-methylpentane-1,5-diamine, pentane-1,3-diamine, cyclohexane-1,3-diyldimethanamine, 2-(aminomethyl)-3,3,5-trimethylcyclopentanamine, 2,2'-oxydiethanamine dihydrochloride, 3,3'-(butane-1,4-diylbis(oxy))bis(propan-1-amine), cyclohexane-1,4-diyldimethanamine, 3,3'-((oxybis(ethane-2,1-diyl))bis(oxy))bis(propan-1-amine), 3,3'-(2,4,8,10-tetraoxaspiro[5,5]undecane-3,9-diyl)bis(propan-1-amine), (2,5-dimethyl-1,4-phenylene)dimethanamine, 3,3'-oxybis(propan-1-amine), (perchloro-1,4-phenylene)dimethanamine, 2,2,3,3,4,4,5,5-octafluorohexane-1,6-diamine, 3,3'-(5H-imidazo[4',5':4,5]benzo[1,2-d]thiazole-2,6-diyl)bis(propan-1-amine), cyclohexane-1,4-diamine, hexahydrofuro[3,2-b]furan-3,6-diamine, 3-(aminomethyl)cyclohexanamine, 4,4'-oxydicyclohexanamine, 3,3'-thiobis(propan-1-amine), 2,2,3,3-tetramethylbutane-1,4-diamine, 2,2'-sulfonyldiethanamine, (2,5-dichloro-1,4-phenylene)dimethanamine, (oxybis(4,1-phenylene))dimethanamine, 2,2'-(2-fluoro-1,3-phenylene)diethanamine, pyridine-2,3-diyldimethanamine, (2-(trifluoromethyl)-1,4-phenylene)dimethanamine, 2,2'-(2,5-dimethoxy-1,4-phenylene)diethanamine, (2-methyl-1,4-phenylene)dimethanamine, 2,2'-(1,4-phenylenebis(oxy))diethanamine, N1-(3-aminopropyl)-N1-methylpropane-1,3-diamine, 1,4-phenylenedimethanamine, and combinations thereof.

Additionally or alternatively, in any of the above aspects of the present disclosure, the aminoalcohol is selected from the group consisting of 2-aminoethanol, 2-amino-2-(hydroxymethyl)propane-1,3-diol, L-ornithin hydrochloride, DL-norepinehrine, 2-(2-aminoethoxy)ethanol, 1-aminopropan-2-ol, 6-aminohexan-1-ol, (3R,4R,5S)-3-amino-6-(hydroxymethyl)tetrahydro-2H-pyran-2,4,5-triol hydrochloride, 2-amino-4-hydroxybutanoic acid, 3-aminopropan-1-ol hydrochloride, (2S,3R,4R,5S)-3-amino-6-(hydroxymethyl)tetrahydro-2H-pyran-2,4,5-triol hydrochloride, 1,3-diaminopropan-2-ol, 4-aminobutan-1-ol, 1-aminobutan-2-ol, 3-aminopropane-1,2-diol, (1R,2R)-2-(aminomethyl)cyclohexanol hydrochloride, 4-aminobutan-2-ol, 3-amino-3-phenylpropan-1-ol, (1S,2S)-2-aminocyclopentanol, 5-amino-2,2-dimethylpentan-1-ol, (1s,4s)-4-aminocyclohexanol hydrochloride, 4-amino-3-hydroxybutanoic acid, 2-amino-1-(4-nitrophenyl)propane-1,3-diol, 2-aminooctadecane-1,3-diol, and combinations thereof.

Additionally or alternatively, in any of the above aspects of the present disclosure, the ascorbic acid isocyanate is formed by contacting ascorbic acid with a diacid and an oxalyl halide.

In additional aspects, the diacid is selected from the group consisting of succinic acid, glutaric acid, adipic acid, heptanedioic acid, octanedioic acid, decanedioic acid, undecanedioic acid, nonanedioic acid, 2-methylsuccinic acid, 2,2'-(1,2-phenylene)diacetic acid, 1,4-(Di-2-carboxy-ethenyl)benzene, 3,3'-(1,4-phenylene)dipropanoic acid, and combinations thereof.

In further aspects, the diacid is of formula:

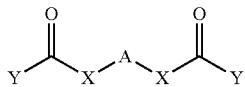

wherein Y is selected from the group consisting of a halogen and a hydroxyl group, A is selected from the group consisting of a carbon atom, a heteroatom, a carbocyclic group, an heterocyclic group, an aromatic group and a non-aromatic group, and X is selected from the group consisting of C1-12, an alkene, and an alkyne.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1A:
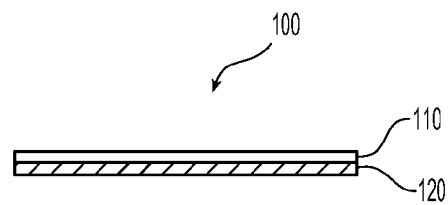
FIG. 1A is a side, cross-sectional view of an implantable medical device according to one embodiment described in the present disclosure.

The present disclosure relates to implantable medical devices which include at least one substrate and at least one biodegradable polymer composition on a portion thereof. The biodegradable polymer composition includes ascorbic acid.

As used herein, the term "biodegradable" in reference to a material shall refer to the property of the material being able to be harmlessly absorbed by the body. In the present application, the terms "biodegradable," "bioresorbable," and "bioabsorbable" are used interchangeably and are intended to mean the characteristic according to which a material decomposes, or loses structural integrity under body conditions (e.g., enzymatic degradation or hydrolysis) or are broken down (physically or chemically) under physiologic conditions in the body, such that the degradation products are excretable or absorbable by the body after a given period of time. The time period may vary, from about one hour to about several months or more, depending on the chemical nature of the material. In embodiments, the material may not be completely absorbed, provided the non-absorbed material poses no health risks and is biocompatible.

By implantable, the medical devices described herein may be positioned, for any duration of time, at a location within a body, such as within a portion of the abdominal cavity. Furthermore, the terms "implantation" and "implanted" refer to the positioning, for any duration of time, of a medical device at a location within a body, such as within a portion of the abdominal cavity.

The present disclosure provides for biodegradable polymer compositions including ascorbic acid, as well as synthesis and use thereof in tissue regeneration and, in particular, abdominal wall regeneration. Tissue regeneration depends on collagen formation within the tissue. One mechanism for collagen formation involves post-translational hydroxylation of various α-amino acids such as proline and lysine. These hydroxylations increase intermolecular cross-linking density of the collagen fibers and their tensile strength. Ascorbic acid is a cofactor in the hydroxylation process. Thus, providing additional ascorbic acid at the tissue site helps increase generation of collagen. As the polymer compositions degrade, sustained release of ascorbic acid occurs, further promoting proline and lysine hydroxylation during the tissue regeneration process.

Ascorbic acid polymer compositions according to the present disclosure may be formed by initially contacting ascorbic acid or derivatives thereof with a diacid to produce an ester acid. The ester acid may then be converted to an isocyanate in a two-step procedure that initially converts the ester acid to a corresponding acyl halide such as acyl chloride by reaction with an oxalyl halide such as oxalyl chloride and converting the acyl halide into an isocyanate by contacting with sodium azide followed by rearrangement of the intermediate acyl azide. The isocyanate substituted ascorbic acid derivatives may then be polymerized with aminoalcohols, polyamines, polyols, and combinations thereof to form polyurethanes, polyureas, and combinations thereof.

Examples of suitable diacids which may be contact with ascorbic acid include, but are not limited to, succinic acid, glutaric acid, adipic acid, heptanedioic acid, octanedioic acid, decanedioic acid, undecanedioic acid, nonanedioic acid, 2-methylsuccinic acid, 2,2'-(1,2-phenylene)diacetic acid, 1,4-(Di-2-carboxy-ethenyl)benzene, 3,3'-(1,4-phenylene)dipropanoic acid, and combinations thereof.

In embodiments, suitable diacids may be of formula (III):

where Y may be a halogen or a hydroxyl group, A may be a carbon atom, a heteroatom, a carbocyclic group, a heterocyclic group, an aromatic group and/or a non-aromatic group, and X may be $C_{1-12}$, an alkene, or an alkyne.

Examples of suitable aminoalcohols which may be contacted with isocyanate substituted ascorbic acid derivatives include, but are not limited to, 2-aminoethanol, 2-amino-2-

(hydroxymethyl)propane-1,3-diol, L-ornithin hydrochloride, DL-norepinehrine, 2-(2-aminoethoxy)ethanol, 1-aminopropan-2-ol, 6-aminohexan-1-ol, (3R,4R,5S)-3-amino-6-(hydroxymethyl)tetrahydro-2H-pyran-2,4,5-triol hydrochloride, 2-amino-4-hydroxybutanoic acid, 3-aminopropan-1-ol hydrochloride, (2S,3R,4R,5S)-3-amino-6-(hydroxymethyl)tetrahydro-2H-pyran-2,4,5-triol hydrochloride, 1,3-diaminopropan-2-ol, 4-aminobutan-1-ol, 1-aminobutan-2-ol, 3-aminopropane-1,2-diol, (1R,2R)-2-(aminomethyl)cyclohexanol hydrochloride, 4-aminobutan-2-ol, 3-amino-3-phenylpropan-1-ol, (1S,2S)-2-aminocyclopentanol, 5-amino-2,2-dimethylpentan-1-ol, (1s,4s)-4-aminocyclohexanol hydrochloride, 4-amino-3-hydroxybutanoic acid, 2-amino-1-(4-nitrophenyl)propane-1,3-diol, 2-aminooctadecane-1,3-diol, and combinations thereof.

Examples of suitable polyamines which may be contacted with isocyanate substituted ascorbic acid derivatives include, but are not limited to, pentane-1,5-diamine, 3,3'-(cyclohexane-1,4-diyl)bis(propan-1-amine), 3-(aminomethyl)-3,5,5-trimethylcyclohexanamine, 1,3-phenylenedimethanamine, butane-1,3-diamine, cyclohexane-1,2-diamine, 2,3,4-trimethylhexane-1,6-diamine, N1-(3-aminopropyl)butane-1,4-diamine, 2-methylpentane-1,5-diamine, pentane-1,3-diamine, cyclohexane-1,3-diyldimethanamine, 2-(aminomethyl)-3,3,5-trimethylcyclopentanamine, 2,2'-oxydiethanamine dihydrochloride, 3,3'-(butane-1,4-diylbis(oxy))bis(propan-1-amine), cyclohexane-1,4-diyldimethanamine, 3,3'-((oxybis(ethane-2,1-diyl))bis(oxy))bis(propan-1-amine), 3,3'-(2,4,8,10-tetraoxaspiro[5,5]undecane-3,9-diyl)bis(propan-1-amine), (2,5-dimethyl-1,4-phenylene)dimethanamine, 3,3'-oxybis(propan-1-amine), (perchloro-1,4-phenylene)dimethanamine, 2,2,3,3,4,4,5,5-octafluorohexane-1,6-diamine, 3,3'-(5H-imidazo[4',5':4,5]benzo[1,2-d]thiazole-2,6-diyl)bis(propan-1-amine), cyclohexane-1,4-diamine, hexahydrofuro[3,2-b]furan-3,6-diamine, 3-(aminomethyl)cyclohexanamine, 4,4'-oxydicyclohexanamine, 3,3'-thiobis(propan-1-amine), 2,2,3,3-tetramethylbutane-1,4-diamine, 2,2'-sulfonyldiethanamine, (2,5-dichloro-1,4-phenylene)dimethanamine, (oxybis(4,1-phenylene))dimethanamine, 2,2'-(2-fluoro-1,3-phenylene)diethanamine, pyridine-2,3-diyldimethanamine, (2-(trifluoromethyl)-1,4-phenylene)dimethanamine, 2,2'-(2,5-dimethoxy-1,4-phenylene)diethanamine, (2-methyl-1,4-phenylene)dimethanamine, 2,2'-(1,4-phenylenebis(oxy))diethanamine, N1-(3-aminopropyl)-N1-methylpropane-1,3-diamine, 1,4-phenylenedimethanamine, and combinations thereof.

Examples of suitable polyols which may be contacted with isocyanate-substituted ascorbic acid derivatives include, but are not limited to, triethanolamine, 2,2'-(butylimino)diethanol, sucrose, 1,4-butanediol, 2,2'-oxybisethanol, D-(+)-Lactose, 1,3-butanediol, butynediol, tetrahydrofuran-2,5-dimethanol, 1,5-pentanediol, D-(+)-glucono-1,5,lactone, diglycerol, N-phenyldiethanolamine, p-xylene glycol, tetraethyleneglycol, N-ethyldiethanolamine, hexahydro-1,3,5-tris(hydroxyethyl)-s-triazine, 1,2-benzenedimethanol, 1,3,5-tris(2-hydroxyethyl)-1,3,5-triazine-2,4,6-trione, 2,2'-[(1-methylethyl)imino]bis-ethanol, 3-hydroxy-2,2-dimethylpropyl 3-hydroxy-2,2-dimethylpropionate, 1,2,6-hexanetriol, ditrimethylol propane, 1,4-piperazinediethanol, 1,4-cyclohexanedimethanol, 1,4-benzenedicarboxylic acid, bis(2-hydroxyethyl) ester, 2-[[1-(hydroxymethyl)propyl]amino]-3-pyridinemethanol, tripentaerythritol, 1-[N,N Bis (2-hydroxyethyl)amino]-2-propanol, hydroquinone bis(2-hydroxyethyl)ether, 1,2-bis(2-hydroxyethoxy)benzene, and combinations thereof.

Embodiments of processes for forming polymer compositions including ascorbic acid are shown in formulas (I) and (II) below.

(I)

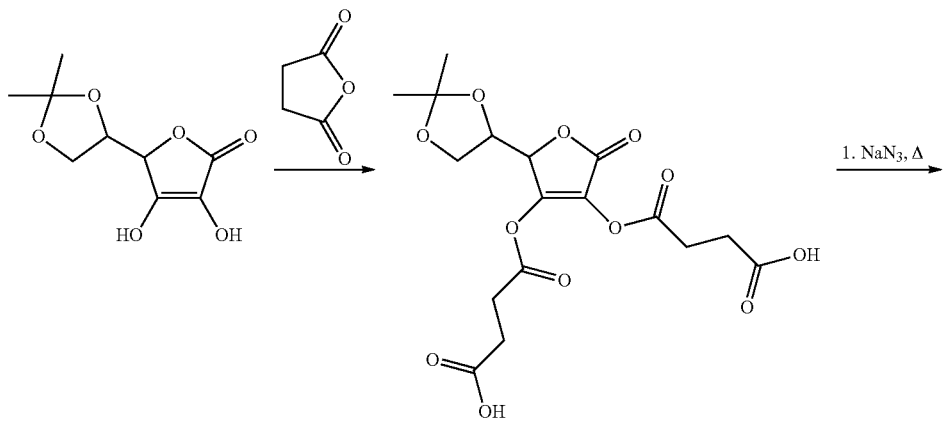

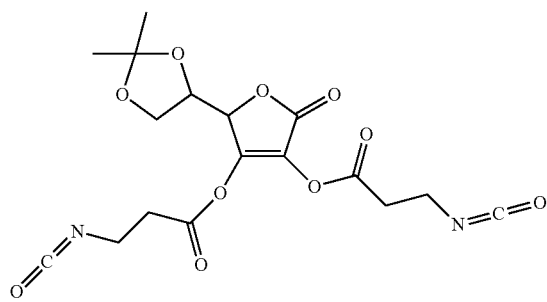

Polyols, polyamines → Polyurethanes and polyureas

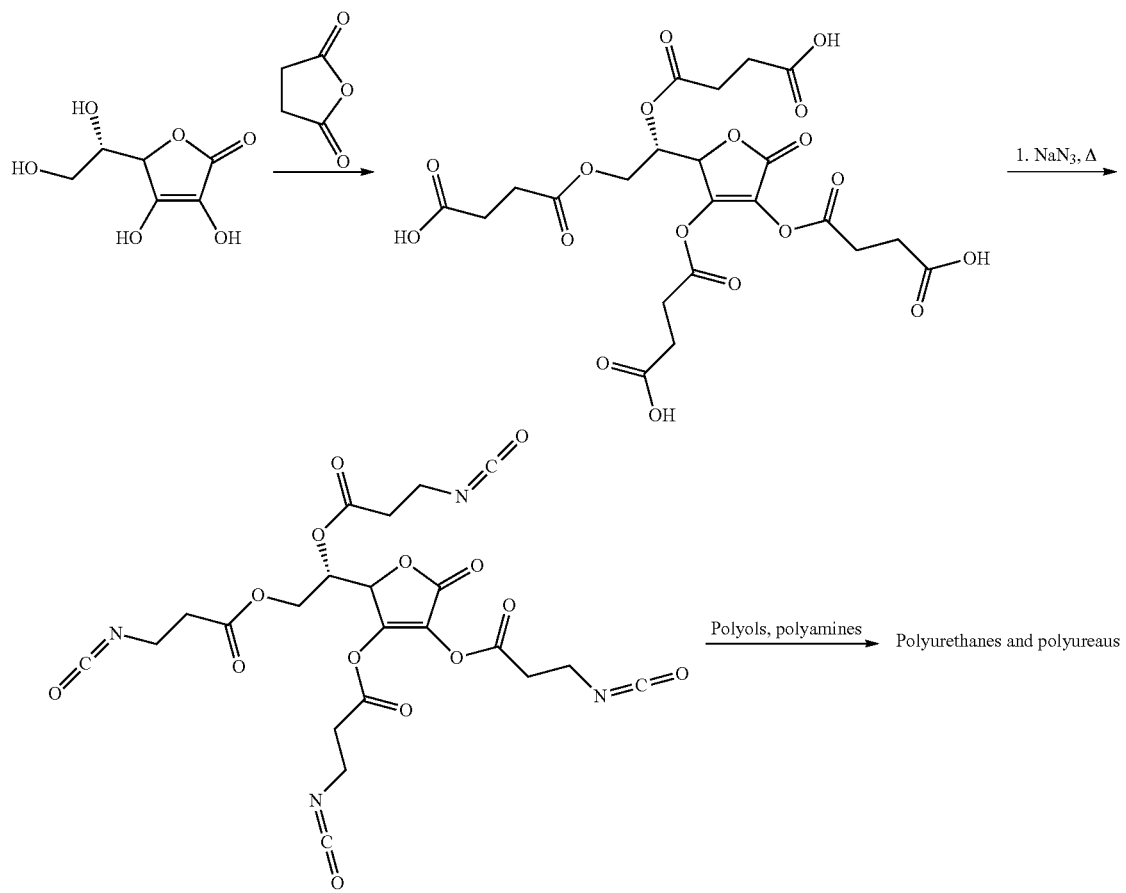

In some embodiments, the polymer composition may include at least one plasticizer, i.e., glycerol, PEG, etc. For instance, the polymer composition may include collagen, and at least one of PEG and glycerol.

The above-described biodegradable polymer ascorbic acid compositions may be applied to a suitable substrate. Such substrates include, but are not limited to, a film, a coating, a sponge, a foam, a mesh, and combinations thereof. The substrate described herein may include porous fabrics made from intertwined filaments. The filaments may be monofilaments or multi-filaments and, in embodiments, a plurality of multi-filaments may be combined to form yarns. The filaments may comprise core/sheath constructs. The filaments may extend horizontally and vertically in a manner which produces sections where the filaments cross-over one another, creating points of common intersection. The surgical mesh may be woven, non-woven, knitted or braided. In some embodiments, the filaments may form two-dimensional or three-dimensional meshes. Some examples of two-dimensional and/or three-dimensional mesh substrates may be found in U.S. Pat. No. 7,021,086, U.S. Pat. No. 6,596,002, and U.S. Pat. No. 7,331,199, the entire disclosures of each of which are incorporated by reference herein.

Figure 1B:
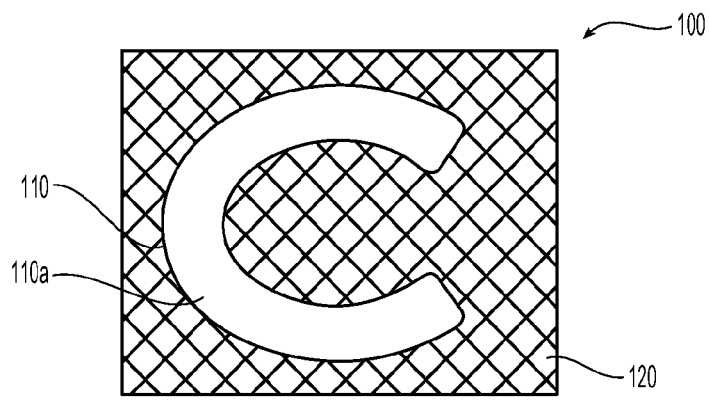
FIG. 1B is a top view of an implantable medical device according to one embodiment of the present disclosure.
Figure 1C:
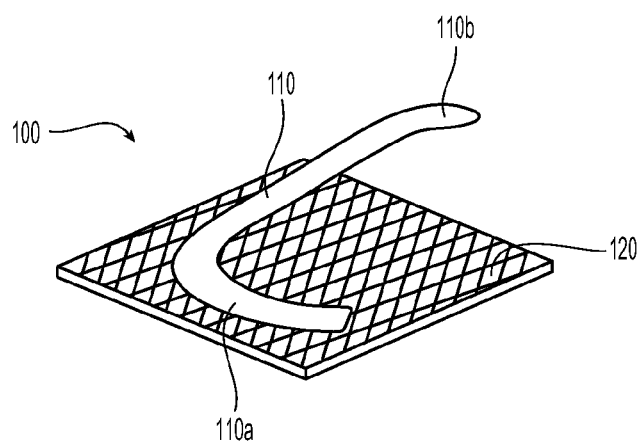
FIG. 1C is a perspective view of the implantable medical device of FIG. 1A with a film extended away from a mesh according to one embodiment of the present disclosure.

Turning now to FIGS. 1A-1C, implantable medical device 100 is illustrated including a polymeric composition shown as a film 110 positioned on a substrate shown as a mesh 120, wherein film 110 covers a portion of the mesh 120. In embodiments, the film 110 may cover the entire surface of the mesh 120 or extend beyond the perimeter thereof. In further embodiments, the film 110 may cover only a portion of the mesh 120 and may have any suitable shape such as, circle, polygonal, Y-shaped, U-shaped, and the like as shown in FIG. 1B With respect to FIGS. 1B and 1C, film 110 includes first portion 110a which is secured to mesh 120 and an unsecured, extendable portion 110b, which may initially be positioned in the same plane as mesh 120 (FIG. 1B). First portion 110a of film 110 may be permanently attached to mesh 120 by any suitable means in the art and as described herein. In some embodiments, extendable portion 110b of film 110 may be movable to extend away form mesh 120 (FIG. 1B). In some embodiments, extendable portion 110b of film 110 may extend away from mesh 120 in a fixed position (FIG. 1C).

The films described herein may be formed by any suitable method within the purview of those skilled in the art. In embodiments, a solution may be formed which includes the suitable polymeric material and any optional ingredients. The solution may be cast, spray coated using an ultrasonic sprayer, extruded, molded and the like, to form the films described herein. Suitable solvents for making polymer solutions include, without limitation, methylene chloride, chloroform, N-methylpyrrolidone, tetrahydrofuran, dimethylformamide, methanol, ethanol, hexanes, acetone, water and combinations thereof.

In some embodiments, the film may be cast directly on a portion of the mesh surface. In other embodiments, the film may be spray coated directly on a portion of the mesh. In still other embodiments, the film may be formed before being connected to the mesh.

In embodiments, the film may be created using a spraying technique, such as ultrasonic spraying. For example, the medical device as described herein may be fabricated by passing one or more solutions containing the polymer(s) materials suitable for forming the film, and optionally one or more therapeutic agents, through an ultrasonic spray nozzle to form droplets. The droplets may be mixed while falling towards or being deposited onto an inert substrate, such as silicone sheet, or a portion of the mesh thereby forming the film or the substrate. In some embodiments, prior to spraying the film, a separate inert substrate may be positioned on a portion of the mesh, preventing film attachment thereon. Thus, upon formation of the film, the film may adhere to the portions of the mesh which were not covered by the inert substrate and the film will not fixedly attach to the portions of the mesh which are covered by the inert substrate. The inert substrate may then be removed from the implant prior to implantation.

The substrate and/or the polymer composition may be preformed or cut into any suitable shape such as, for example, round, square, star shaped, octagonal, rectangular, polygonal, triangle, u-shaped, and/or oval.

Suitable meshes for use in the present disclosure include, for example, a collagen composite mesh such as PARIETEX™ Composite Mesh (commercially available from Covidien). PARIETEX™ Composite Mesh is a 3-dimensional polyester weave with a resorbable collagen film bonded on one side. Another suitable mesh includes PARIETEX PROGRIP™ self-fixating mesh (also commercially available from Covidien). PARIETEX PROGRIP™ is a polyester mesh which includes poly lactic acid (PLA) grip members. Other suitable meshes include those sold under the names PARIETENE®, SURGIPRO™ (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C. R. Bard, Inc.); PROLITE™, PROLITE ULTRA™ (all commercially available from Atrium Medical); COMPOSIX®, SEPRAMESH®, and VISILEX® (all commercially available from Davol, Inc.); and DUALMESH®, MYCROMESH®, and INFINIT® mesh (all commercially available from W. L. Gore). Additionally, meshes within the scope and context of this disclosure may include biologic materials such as allografts (i.e., ALLODERM® Regenerative Tissue Matrix from Lifecell), autografts, and xenografts (i.e., PERMACOL™, from Covidien). In alternate embodiments, processed/purified tissues may also be employed. In embodiments, PARIETEX™ Composite Mesh or PARIETEX™ Pro-grip may be utilized in accordance with the present invention.

Any biocompatible material may be used to form the mesh described herein. For example, the mesh may be made from non-bioabsorbable materials, such as polypropylene, polyethylene terephthalate, polytetrafluoroethylene, combinations thereof, and the like. In other examples, the mesh may be made from bioabsorbable materials, such as polylactide, polyglycolide, polycaprolactone, polydioxanone, polysaccharides, combinations thereof, and the like. In embodiments, the mesh may be made from a combination of absorbable and non-bioabsorbable materials.

The medical devices described herein further include a secondary film layer which may be made from any biocompatible material. The biocompatible material may be a homopolymer or a copolymer, including random copolymer, block copolymer, or graft copolymer. The biocompatible material may be a linear polymer, a branched polymer, or a dendrimer. The biocompatible material may be of natural or synthetic origin. The biocompatible material may be bioabsorbable or non-bioabsorbable.

Some non-limiting examples of bioabsorbable materials used to form the secondary film include polymers selected from the group consisting of aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, aliphatic polyesters include, but are not limited to, homopolymers and copolymers of lactide (including lactic acid, D-,L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable bioabsorbable materials may include but are not limited to poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; mucilage, pectin; and combinations thereof.

Both the substrate and/or the polymer composition thereon may further include at least one optional ingredient in addition to ascorbic acid. Some examples of suitable optional ingredients include emulsifiers, viscosity enhancers, dyes, pigments, fragrances, pH modifiers, wetting agents, plasticizers, antioxidants, and the like. The optional ingredients may represent up to about 10% of the substrate and/or the polymer composition by weight.

The implantable medical devices of the present disclosure may include at least one therapeutic agent in addition to ascorbic acid. The therapeutic agent may be included in any portion of the implant including the substrate and/or the polymer ascorbic acid composition. The term "therapeutic agent", as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic affect, such as, anti-adhesives, antimicrobials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents, which may be included as a drug include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable agents, which may be included in the devices described herein include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

Some specific non-limiting examples of water-soluble drugs that may be used in the present implantable devices include, lidocaine, bupivicaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenyloin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cyclothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof.

In some embodiments, the therapeutic agent may include an anesthetic, i.e., bupivicaine, lidocaine, benzocaine, and the like.

Although the above therapeutic agents have been provided for the purposes of illustration, it should be understood that the present disclosure is not so limited. In particular, although certain therapeutic agents are specifically referred to above, the present disclosure should be understood to include analogues, pro-drugs, derivatives and conjugates of such agents.

The implants described herein may be useful in many endoscopic, laparoscopic, arthroscopic, endoluminal, transluminal, and/or open surgical procedures. Some examples include hernia repair, repair of vaginal prolapse, ligament repair, tendon repair, and the like.

It will be understood that various modifications may be made to the embodiments disclosed herein. For example, in embodiments the medical device may be folded prior to being delivered into the body via a cannula, trocar or laparoscopic delivery device. In another example, the medical devices described herein may be sterilized and packaged into using any suitable sterilization process, i.e., gamma radiation, and any suitable medical device package, i.e., an injectable medical device package. In still other examples, the implants described herein may include more than one film, mesh, finger, extended portion, and/or therapeutic agent. Thus, those skilled in the art will envision other modifications within the scope and spirit of the claims.

What is claimed is:

1. An implantable medical device comprising:
   a substrate selected from the group consisting of a film, a coating, a sponge, a foam, a mesh, and combinations thereof; and
   a film comprising a polymer composition comprising ascorbic acid ester isocyanate and a monomer selected from the group consisting of a polyol, a polyamine, an aminoalcohol, and combinations thereof, the polymer composition disposed on at least a portion of the substrate.

2. The implantable medical device according to claim 1, further comprising at least one therapeutic agent.

3. The implantable medical device according to claim 1, wherein the polymer composition comprises a polymer selected from the group consisting of polyurethanes, polyureas, and combinations thereof.

4. The implantable medical device according to claim 1, wherein the polyamine is selected from the group consisting of pentane-1,5-diamine, 3,3'-(cyclohexane-1,4-diyl)bis(propan-1-amine), 3-(aminomethyl)-3,5,5-trimethylcyclohexanamine, 1,3-phenylenedimethanamine, butane-1,3-diamine, cyclohexane-1,2-diamine, 2,3,4-trimethylhexane-1,6-diamine, N1-(3-aminopropyl)butane-1,4-diamine, 2-methylpentane-1,5-diamine, pentane-1,3-diamine, cyclohexane-1,3-diyldimethanamine, 2-(aminomethyl)-3,3,5-trimethylcyclopentanamine, 2,2'-oxydiethanamine dihydrochloride, 3,3'-(butane-1,4-diylbis(oxy))bis(propan-1-amine), cyclohexane-1,4-diyldimethanamine, 3,3'-((oxybis(ethane-2,1-diyl))bis(oxy))bis(propan-1-amine), 3,3'-(2,4,8,10-tetraoxaspiro[5,5]undecane-3,9-diyl)bis(propan-1-amine), (2,5-dimethyl-1,4-phenylene)dimethanamine, 3,3'-oxybis(propan-1-amine), (perchloro-1,4-phenylene)dimethanamine, 2,2,3,3,4,4,5,5-octafluorohexane-1,6-diamine, 3,3'-(5H-imidazo[4',5':4,5]benzo[1,2-d]thiazole-2,6-diyl)bis(propan-1-amine), cyclohexane-1,4-diamine, hexahydrofuro[3,2-b]furan-3,6-diamine, 3-(aminomethyl)cyclohexanamine, 4,4'-oxydicyclohexanamine, 3,3'-thiobis(propan-1-amine), 2,2,3,3-tetramethylbutane-1,4-diamine, 2,2'-sulfonyldiethanamine, (2,5-dichloro-1,4-phenylene)dimethanamine, (oxybis(4,1-phenylene))dimethanamine, 2,2'-(2-fluoro-1,3-phenylene)diethanamine, pyridine-2,3-diyldimethanamine, (2-(trifluoromethyl)-1,4-phenylene)dimethanamine, 2,2'-(2,5-dimethoxy-1,4-phenylene)diethanamine, (2-methyl-1,4-phenylene)dimethanamine, 2,2'-(1,4-phenylenebis(oxy))diethanamine, N1-(3-aminopropyl)-N1-methylpropane-1,3-diamine, 1,4-phenylenedimethanamine, and combinations thereof.

5. The implantable medical device according to claim 1, wherein the aminoalcohol is selected from the group consisting of 2-aminoethanol, 2-amino-2-(hydroxymethyl)propane-1,3-diol, L-ornithin hydrochloride, DL-norepinehrine, 2-(2-aminoethoxyl)ethanol, 1-aminopropan-2-ol, 6-aminohexan-1-ol, (3R,4R,5S)-3-amino-6-(hydroxymethyl)tetrahydro-2H-pyran-2,4,5-triol hydrochloride, 2-amino-4-hydroxybutanoic acid, 3-aminopropan-1-ol hydrochloride, (2S,3R,4R,5S)-3-amino-6-(hydroxymethyl)tetrahydro-2H-pyran-2,4,5-triol hydrochloride, 1,3-diaminopropan-2-ol, 4-aminobutan-1-ol, 1-aminobutan-2-ol, 3-aminopropane-1,2-diol, (1R,2R)-2-(aminomethyl)cyclohexanol hydrochloride, 4-aminobutan-2-ol, 3-amino-3-phenylpropan-1-ol, (1S,2S)-2-aminocyclopentanol, 5-amino-2,2-dimethylpentan-1-ol, (1s,4s)-4-aminocyclohexanol hydrochloride, 4-amino-3-hydroxybutanoic acid, 2-amino-1-(4-nitrophenyl)propane-1,3-diol, 2-aminooctadecane-1,3-diol, and combinations thereof.

6. The implantable medical device according to claim 1, wherein the ascorbic acid ester isocyanate is formed by contacting ascorbic acid initially with a diacid and subsequently with an oxalyl halide.

7. The implantable medical device according to claim 6, wherein the diacid is selected from the group consisting of succinic acid, glutaric acid, adipic acid, heptanedioic acid, octanedioic acid, decanedioic acid, undecanedioic acid, nonanedioic acid, 2-methylsuccinic acid, 2,2'-(1,2-phenylene)diacetic acid, 1,4-(Di-2-carboxy-ethenyl)benzene, 3,3'-(1,4-phenylene)dipropanoic acid, and combinations thereof.

8. The implantable medical device according to claim 6, wherein the diacid is of formula:

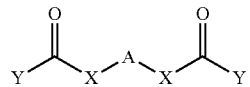

wherein Y is selected from the group consisting of a halogen and a hydroxyl group, A is selected from the group consisting of a carbon atom, a heteroatom, a carbocyclic group, an hetercyclic group, an aromatic group and a non-aromatic group, and X is selected from the group consisting of $C_{1-12}$, an alkene, and an alkyne.

9. An implantable medical device comprising:
   a substrate; and
   a film comprising a polymer composition that is comprised of a polymer selected from the group consisting of polyurethanes, polyureas, and combinations thereof, the polymer comprising:
   an ascorbic acid ester isocyanate; and
   a monomer selected from the group consisting of a polyol, a polyamine, an aminoalcohol, and combinations thereof,
   wherein the polymer composition is disposed on at least a portion of the substrate.

10. The implantable medical device according to claim 9, wherein the polymer composition comprises a film.

11. The implantable medical device according to claim 9, wherein the substrate is selected from the group consisting of a film, a coating, a sponge, a foam, a mesh, and combinations thereof.

12. The implantable medical device according to claim 9, further comprising at least one therapeutic agent.

13. The implantable medical device according to claim 9, wherein the polyamine is selected from the group consisting of pentane-1,5-diamine, 3,3'-(cyclohexane-1,4-diyl)bis(propan-1-amine), 3-(aminomethyl)-3,5,5-trimethylcyclohexanamine, 1,3-phenylenedimethanamine, butane-1,3-diamine, cyclohexane-1,2-diamine, 2,3,4-trimethylhexane-1,6-diamine, N1-(3-aminopropyl)butane-1,4-diamine, 2-methylpentane-1,5-diamine, pentane-1,3-diamine, cyclohexane-1,3-diyldimethanamine, 2-(aminomethyl)-3,3,5-trimethylcyclopentanamine, 2,2'-oxydiethanamine dihydrochloride, 3,3'-(butane-1,4-diylbis(oxy))bis(propan-1-amine), cyclohexane-1,4-diyldimethanamine, 3,3'-((oxybis(ethane-2,1-diyl))bis(oxy))bis(propan-1-amine), 3,3'-(2,4,8,10-tetraoxaspiro[5,5]undecane-3,9-diyl)bis(propan-1-amine), (2,5-dimethyl-1,4-phenylene)dimethanamine, 3,3'-oxybis(propan-1-amine), (perchloro-1,4-phenylene)dimethanamine, 2,2,3,3,4,4,5,5-octafluorohexane-1,6-diamine, 3,3'-(5H-imidazo[4',5':4,5]benzo[1,2-d]thiazole-2,6-diyl)bis(propan-1-amine), cyclohexane-1,4-diamine, hexahydrofuro[3,2-b]furan-3,6-diamine, 3-(aminomethyl)

cyclohexanamine, 4,4'-oxydicyclohexanamine, 3,3'-thiobis(propan-1-amine), 2,2,3,3-tetramethylbutane-1,4-diamine, 2,2'-sulfonyldiethanamine, (2,5-dichloro-1,4-phenylene)dimethanamine, (oxybis(4,1-phenylene))dimethanamine, 2,2'-(2-fluoro-1,3-phenylene)diethanamine, pyridine-2,3-diyldimethanamine, (2-(trifluoromethyl)-1,4-phenylene)dimethanamine, 2,2'-(2,5-dimethoxy-1,4-phenylene)diethanamine, (2-methyl-1,4-phenylene)dimethanamine, 2,2'-(1,4-phenylenebis(oxy))diethanamine, N1-(3-aminopropyl)-N1-methylpropane-1,3-diamine, 1,4-phenylenedimethanamine, and combinations thereof.

14. The implantable medical device according to claim 9, wherein the aminoalcohol is selected from the group consisting of 2-aminoethanol, 2-amino-2-(hydroxymethyl)propane-1,3-diol, L-ornithin hydrochloride, DL-norepinehrine, 2-(2-aminoethoxyl)ethanol, 1-aminopropan-2-ol, 6-aminohexan-1-ol, (3R,4R,5S)-3-amino-6-(hydroxymethyl)tetrahydro-2H-pyran-2,4,5-triol hydrochloride, 2-amino-4-hydroxybutanoic acid, 3-aminopropan-1-ol hydrochloride, (2S,3R,4R,5S)-3-amino-6-(hydroxymethyl)tetrahydro-2H-pyran-2,4,5-triol hydrochloride, 1,3-diaminopropan-2-ol, 4-aminobutan-1-ol, 1-aminobutan-2-ol, 3-aminopropane-1,2-diol, (1R,2R)-2-(aminomethyl)cyclohexanol hydrochloride, 4-aminobutan-2-ol, 3-amino-3-phenylpropan-1-ol, (1S,2S)-2-aminocyclopentanol, 5-amino-2,2-dimethylpentan-1-ol, (1s,4s)-4-aminocyclohexanol hydrochloride, 4-amino-3-hydroxybutanoic acid, 2-amino-1-(4-nitrophenyl)propane-1,3-diol, 2-aminooctadecane-1,3-diol, and combinations thereof.

15. The implantable medical device according to claim 9, wherein the ascorbic acid ester isocyanate is formed by contacting ascorbic acid initially with a diacid and subsequently with an oxalyl halide.

16. The implantable medical device according to claim 15, wherein the diacid is selected from the group consisting of succinic acid, glutaric acid, adipic acid, heptanedioic acid, octanedioic acid, decanedioic acid, undecanedioic acid, nonanedioic acid, 2-methylsuccinic acid, 2,2'-(1,2-phenylene)diacetic acid, 1,4-(Di-2-carboxy-ethenyl)benzene, 3,3'-(1,4-phenylene)dipropanoic acid, and combinations thereof.

17. The implantable medical device according to claim 15, wherein the diacid is of formula:

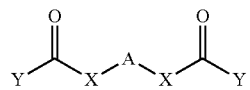

wherein Y is selected from the group consisting of a halogen and a hydroxyl group, A is selected from the group consisting of a carbon atom, a heteroatom, a carbocyclic group, an hetercyclic group, an aromatic group and a non-aromatic group, and X is selected from the group consisting of $C_{1-12}$, an alkene, and an alkyne.

18. A method for forming an implantable medical device comprising:
reacting an ascorbic acid ester isocyanate with a monomer selected from the group consisting of a polyol, a polyamine, an aminoalcohol, and combinations thereof to form a polymer selected from the group consisting of polyurethanes, polyureas, and combinations thereof; and
contacting a substrate with a polymer composition comprising the polymer, such that the polymer composition is disposed on at least a portion of the substrate.

* * * * *